United States Patent
Macovski et al.

[11] Patent Number: 5,835,995
[45] Date of Patent: Nov. 10, 1998

[54] LOCALIZED PULSED SUPERCONDUCTIVE MRI SYSTEM

[76] Inventors: Albert Macovski, 2505 Alpine Rd.; Steven Conolly, 843 Roble Ave., #2, both of Menlo Park, Calif. 94025

[21] Appl. No.: 738,535

[22] Filed: Oct. 28, 1996

[51] Int. Cl.⁶ .................................................. G01V 3/00
[52] U.S. Cl. ................................. 324/309; 324/307
[58] Field of Search .......................... 324/309, 307, 324/306, 312, 314, 300, 322

[56] References Cited

U.S. PATENT DOCUMENTS 4,573,015  2/1986  Abe et al. .............................. 324/309
5,057,776  10/1991  Macovski ............................... 324/309
5,629,624  5/1997  Carlson et al. ......................... 324/309

Primary Examiner—Louis M. Arana

[57] ABSTRACT

A pulsed strong magnetic field, created with a superconductive coil, is applied to a selected region of the anatomy. Following the pulse a relatively low readout field is used along with a set of spatially orthogonal gradient fields parallel to the readout field. The readout field is chosen such that the noise arises primarily from body losses, and results in negligible susceptibility effects. Following excitation, the resultant signals from the precessing moments are detected, processed and used to make magnetic resonance images of the object. The field pulsing is made efficient using energy recovery.

10 Claims, 2 Drawing Sheets

LOCALIZED PULSED SUPERCONDUCTIVE MRI SYSTEM

BACKGROUND OF THE INVENTION

1. Field of the Invention

This invention relates primarily to magnetic resonance imaging systems. In a primary application this invention relates to the use of a pulsed polarizing field using a superconductive coil.

2. Description of Prior Art

Magnetic Resonance Imaging has become one of the wider-used modalities in the field of medical imaging. A descriptive series of papers on NMR imaging appeared in the June 1980 series of the IEEE Transactions on Nuclear Science, Vol. NS-27, pp1220–1255. The basic concepts are covered in the lead article "Introduction to the Principles of NMR" by W. V. House, pp. 1220–1226.

In general, in an MRI imaging system, the object being studied is within a highly-uniform intense static magnetic field. The object is then excited by a high-power radio frequency burst which causes the magnetic moments in the object, which were lined up with the static field, to precess normal to the static field. Using spatially orthogonal gradients, these magnetic moments become spatially varying. A receiver coil picks up the signals from the precessing moments. This signal is processed to create images of the magnetic moment density in the object.

These systems have a number of theoretical and practical problems. The signal to noise ratio is determined by the product of the magnetic field, the voxel volume and the square root of the imaging time. Therefore, if it is desired to have high resolution, as in imaging the coronary arteries, it is necessary to increase the magnetic field and/or the imaging time. Cardiac and respiratory motion make it difficult to increase the imaging time, so the solution appears to be a significantly increased field strength.

This is fraught with many problems. A high field requires a high excitation and readout frequency resulting in severe penetration and heat-deposition problems. Also anything in the object which modifies the magnetic field, such as materials within the body which have changes in magnetic susceptibility, especially metal implants, can seriously distort the image or make imaging impossible. Slightly differing magnetic resonances from different materials, primarily water and fat, can become translated from each other, distorting the image. MRI machines cause loud sounds when the gradient coils are excited in the presence of a strong magnetic field.

One attempt at a simpler system is given in a paper by J. Stepisnik, M. Kos, and V. Erzen in Proc. of XXII Congress Ampere, Roma, 512, 1986. Here the magnetic field is pulsed and then the magnetic moments are allowed to line up in the earth's field. Following this, an r.f. excitation is used to rotate the moments, with a set of gradients in the same direction as the earth's field used to create an image. Another use of a pulsed system is described in U.S. Pat. No. 5,057,776 issued to Albert Macovski. In both of these, a resistive magnet is used to create the pulsed field. The resultant heat dissipation prevents a significantly high magnetic field to be produced.

SUMMARY OF THE INVENTION

An object of this invention is to produce NMR images of an object, such as the body, with high resolution and immunity to variations in the magnetic fields.

A further object of this invention is to avoid the distorting effects of materials with magnetic susceptibility.

A further object of this invention is to avoid the loud sounds caused by gradient coils.

A further object of this invention is to enable the use of stronger magnetic fields, for improved images, without the heating and penetration problems.

A further object of this invention is to provide a strong pulsed magnetic field without excessive heating and losses.

A further object of this invention is to provide an efficient and flexible method of creating a pulsed polarizing field.

A further object of this invention is to provide a method of imaging the heart with high spatial resolution.

Briefly, in accordance with the invention, a pulsed magnetic field is applied to a local region of the body using a superconductive coil. Following the pulse, the polarized magnetic moments are excited and read out in the presence of a readout field and gradient fields. The resultant signals are processed to provide an image of the excited region. To efficiently provide the polarizing field an energy recovery system is used a storage capacitor.

BRIEF DESCRIPTION OF THE DRAWINGS

For a more complete description of the invention, reference can be made to the following detailed description of several illustrative embodiments thereof which is given in conjunction with the accompanying drawings, of which.

DESCRIPTION OF THE PREFERRED EMBODIMENT

Figure 1:
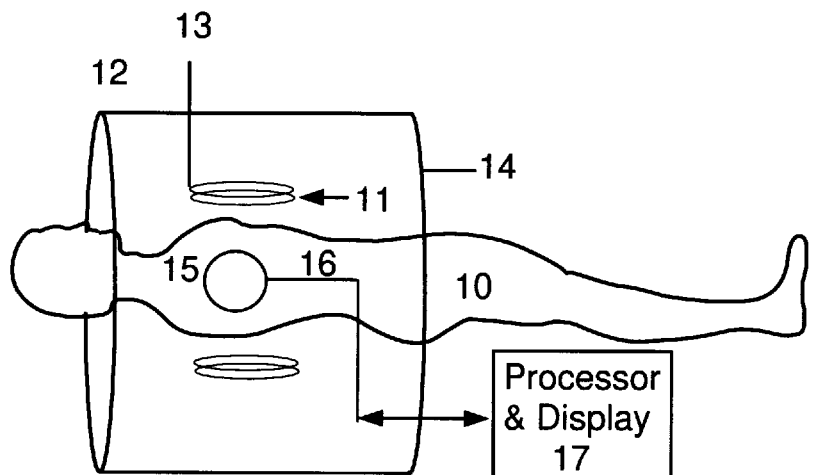
FIG. 1 is a schematic drawing illustrating an embodiment of the invention.
Figure 5:
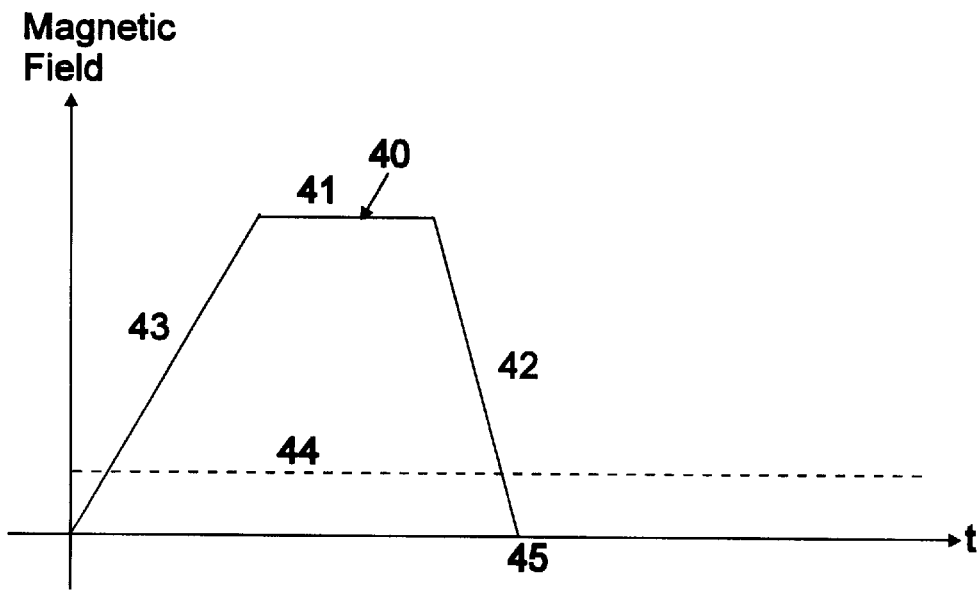
FIG. 5 is a set of waveforms for an embodiment of the invention.

An understanding of the broad aspects of the invention may best be had by reference to FIG. 1. Here it is desired to create a magnetic resonance image of a local region of object 10, such as the heart. In most MRI (magnetic resonance imaging) systems the object 10 would be immersed within an ultra-uniform static magnetic field. If this field is made sufficiently high to create the desired resolution in a reasonable time, it will have to be approximately 3–7 Tesla. At these fields the system would have fundamental problems including penetration of the r.f. field, excessive heat due to the excitation field, severe distortion and limited readout times due to susceptibility and inhomogeneity, and excessive acoustic gradient noise. A pulsed magnetic field is used to polarize the magnetic moments in a local region in 10 by applying a current pulse to superconductive coils 11 where the upper and lower portion of coils 11 are series aiding, not shown. This current pulse 40 is illustrated in FIG. 5. The details of the pulse will subsequently be described.

During the pulse, the magnetic moments in 10 are polarized in the vertical direction parallel to the axis of coils 11. Following the pulse, the magnetic moments will line up in the direction of the readout field created by coil 12. In FIG. 1 the readout field is in quadrature with the polarizing field. Therefore, as long as the field is turned off adiabatically, where $dB/dt << \gamma B^2$, the magnetic moments will follow the magnetic field and rotate 90 degrees and line up parallel to the axis of coil 11. Therefore the turnoff waveform segment 42 in FIG. 5 must meet the adiabatic requirement specified above. In addition to the adiabatic requirement on the turnoff waveform segment 42, both the turn-on and turnoff segments 42 and 43 must meet the $dB/dt$ requirements to avoid neural stimulation which is approximately 20 Tesla per second. This limitation is primarily based on gradient waveforms which reach their greatest intensity in the body extremities such as the hands and result in tingling and discomfort. It is anticipated that a field of the type created by coil 11 which falls off rapidly outside of the magnetized region will not cause any problems and will tolerate much larger values of $dB/dt$.

Figure 2:
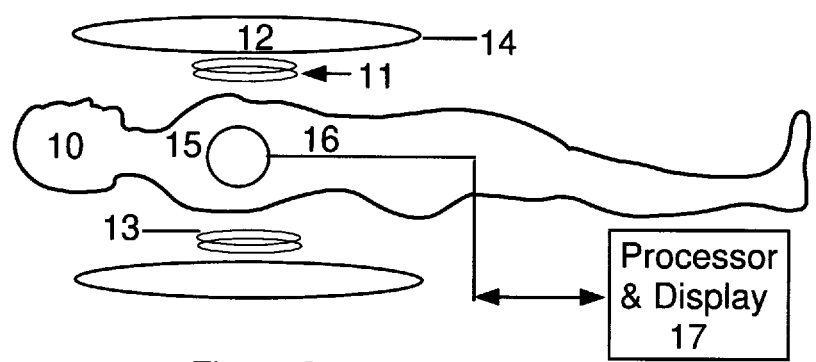
FIG. 2 is a schematic drawing illustrating an alternate embodiment of the invention.

An alternate approach is illustrated in FIG. 2. Here the polarizing coil is identical but the readout coils 12 are now large pancake shaped coils which are co-axial with the polarizing coils 11 creating a readout field in the same direction. The adiabatic requirement is no longer necessary since, in any case, the polarized moments will remain pointing along the axis of coils 11 and 12 following the polarizing pulse. The $dB/dt$ requirement, however, must be observed.

The waveform requirements for the polarizing pulse are shown in waveform 40 in FIG. 5. The rising portion is relatively non-critical and can be chosen based on the type of superconductive materials used in coils 11. In some cases a slower rise time helps to keep the conductor in a stable state. In segment 41 the current is through the coils is kept at a relatively constant level while the magnetic moments are polarized at a rate T1. This duration can be adjusted to determine the relative sensitivity of the image to T1. If segment 41 is made long as compared to all of the T1 values, then all magnetic moments will approach their full amplitude with little or no T1 sensitivity. If segment 41 is made relatively short, materials with short T1 values will reach near full amplitude while those with relatively long T1 values will have low recovery, resulting in large T1 contrast. Segment 43 also contributes to the T1 sensitivity. Durations of segments 43 plus 41 will be in the range of 0.2 to 1.5 seconds. Segment 42, as previously described, must meet the adiabatic requirement and the $dB/dt$ requirement. A typical value for a 5 Tesla pulse would be approximately 200 msec.

Readout coils 12 are supplied by d.c. current waveform 44 which is significantly lower than the pulse amplitude. Typical values for this field are 0.03–0.3 Tesla. The lower this value, the greater the immunity to susceptibility and inhomogeneity errors. However, if the value is excessively low, the coil losses can become comparable to or exceed the body losses, thus diminishing the SNR. This can be helped by cooling the coil or using a superconductive coil.

The required energy for the polarizing coils 11 is considerably reduced by using relatively small coils to energize a relatively small region of the body; such as the heart. The pulsed arrangement of itself enables the use of the smaller coils since, in the polarizing function, homogeneity is not important and extensive variations can be readily tolerated. However, for the high fields desired, even the small volume represents a significant amount of energy, of the order of 100–1000 joules. It is therefore important to use an energy recovery system to supply the pulse power. The fact that the coil is lossless greatly facilitates the use of an energy recovery system. In previously referenced U.S. Pat. No. 5,057,776, a resonant system was shown to increase the efficiency. However, this limited the waveform to a sinusoid and did not allow for variations in duration.

Figure 3:
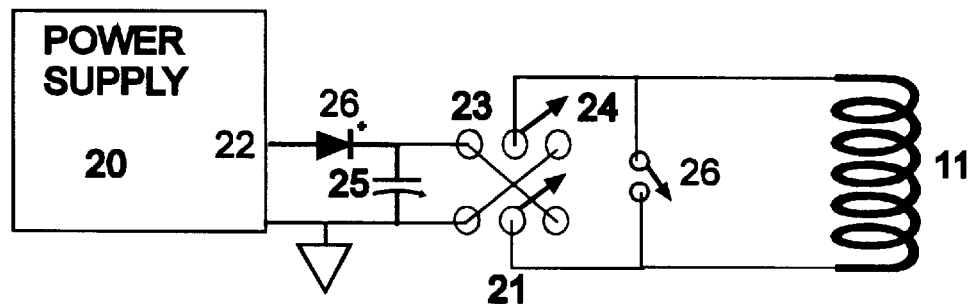
FIG. 3 is a schematic drawing of the energy-recovery pulsing system of the invention.

The energy recovery system is shown in FIG. 3. Initially, d.c. voltage 22 from power supply 20 charges storage capacitor 25 through diode 26. The pulse is initiated by turning switch 21 to position 23 on the left, thus connecting coil 11 to the d.c. voltage. This generates segment 43 by proving a current ramp where $di/dt = E/L$ where E is voltage 22 and L is the inductance of coils 11. When the desired field is reached, switch 21 is put in a neutral, non-contact position and switch 26 is turned on shorting coil 11 and maintaining the peak current for segment 41. Following this segment switch 26 is opened and switch 21 is moved to the right to position 24, applying a reversed voltage -E from capacitor 25 to coils 11, providing downramp 42. During this process the charge removed from capacitor 25 during segment 43 is now returned to the capacitor providing energy recovery. When segment 42 reaches zero, switch 21 is opened, maintaining zero current in coils 11. To insure that the current does not go negative an additional diode, not shown, can be placed in series with coils 11. Any energy lost during this process is provided by power supply 20. The value of capacitor 25 is chosen to have a negligible change during the current pulse. The voltage change across the capacitor is given by $$\Delta E = \frac{IT}{C}$$

Allowing for 500 volt drop in 0.2 seconds using a 500 ampere ramp requires a capacitor of 50,000 $\mu$fd at 2,500 volts. These values are based on the representative system derived subsequently.

Figure 4:
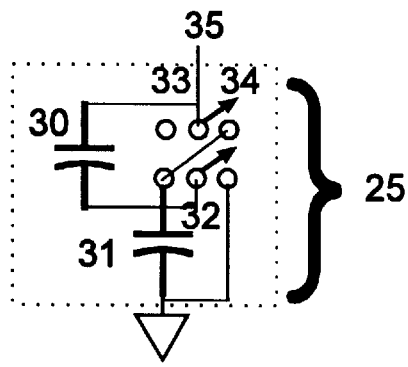
FIG. 4 is a schematic diagram of an alternate embodiment of the energy-recovery system.

The preceding described system will have the rising and falling segments 43 and 42 with the same duration. In some cases it may be desired to have rises and falls of differing slopes. For example, with some superconductive materials it is desired to have a relatively slow ramp-up interval. This is provided in the system of FIG. 4. Here the system of switches and capacitors replaces capacitor 25 in FIG. 3. When switch 34 is on the right, in position 34, identical capacitors 30 and 31 are in parallel. They will then be charged by power supply 22 and used to control the current rise, segment 43, at the desired rate. However, this rate may be too slow for the downramp 42. This segment should not be too slow to avoid a loss of magnetization. On the downramp switch 32 is thrown to the left to position 33 placing the two capacitors in series, doubling the voltage and doubling the rate of decay. Using the values given above, each of the capacitors, 30 and 31, would be 25,000 $\mu$fd. This same process can be used to provide three or more capacitors going from the parallel to the series configuration.

All of the switches are shown schematically as mechanical switches. In reality these would be electronic switches such as SCR's (silicon controlled rectifiers), thyristors or comparable high-power devices. These switches are actuated by a pre-set computer program as in all MRI systems used today. With cardiac studies, which is one of the primary uses of this invention, the switches would be timed to the cardiac cycle using a signal derived from the beating heart such as the electrocardiogram. When making a static image of the heart, as with a coronary angiogram, the system is timed to an appropriate part of the heart cycle and repeated until all of k-space is scanned. If a dynamic study is made, as with a ventriculogram, a series of images are made representing different times in the cardiac cycle. These are then played back in the form of a movie.

Following time 45 in FIG. 5, the MRI signal is read out in conventional fashion. First the desired region is excited with an r.f. excitation to cause the polarized moments to precess. An r.f. burst is generated in processor 17 at the readout frequency and applied to coil 15. Although the same coil 15 is shown for excitation and readout, different coils can be used. Following excitation a system of magnetic gradients are used in conventional fashion and are not shown. In FIG. 1 the gradient windings are wound on the same form as readout coil 12. Similarly, in FIG. 2 the gradients are flat and are alongside readout coil 12. Either a 2D or 3D readout can be used. Since susceptibility is not a problem, much longer readouts, of the order of 100 msec., can be used with this system than in conventional systems. Therefore, more of k-space is covered in each readout, requiring fewer heartbeats to create an image. This insures that all of the desired data can be collected in a breath-holding interval, avoiding any motion blurring.

While the gradients are played out, signal 16 is received and demodulated using synchronous detectors in processor 17 in conventional fashion. The demodulated signals are stored as a Fourier transform, and then inverse transformed to provide the desired image which is then displayed.

Coils 11 are designed to provide the desired high field of the order of 5 Tesla. The formula for the B field is given by:

$$B = \frac{\mu N I r_0^2}{2(r_0^2 + z_0^2)^{3/2}}$$

where N is the total number of turns, I is the current, $\mu$ is the permeability, $r_o$ is the radius of the coil and $z_O$ is the axial distance to the coil. Using a radius of 8 cm. and a spacing between coils of 20 cm., the current required for a B=5 Tesla field is given by $$I \approx \frac{2.5 \times 10^6}{N}$$

The voltage E across the coil resulting from the rampdown of approximately 200 msec is given by:

$$E = N\frac{d\phi}{dt} = N\frac{B\pi r_0^2}{2\text{ sec}} = .5N$$

Using these equations the number of turns N can be manipulated depending on the materials and geometry of the coil and the switch requirements. The product of the peak current and peak voltage is independent of N. Some representative values are:
N=5,000 turns total on both coils
I=500 amps
E=2,500 volts
These values can be switched using various varieties of thyristors including reverse blocking and reverse conducting. If the value of the field is lowered, both the peak current and peak voltage are lowered accordingly. Similarly, these are both lowered when the size of the magnetized region is reduced. It is this relatively small size that enables a large magnetic field to be turned on and off with reasonable components.

Although an exemplary system has been described, many variations can be used in this same general theme. For example, readout coil 12 can also been made superconductive if it is desired to make this field somewhat higher. The current 44 in the readout coil applied to terminal 14 can be made controllable. It can be increased to enable the system to operate in a conventional mode, without the pulsed polarizing field, for more general applications with large fields of view such as abdominal or spinal imaging. This would make the instrument versatile, enabling it to provide high performance in local areas, such as the heart and knees, and general performance in other regions.

Instead of the arrangement described, resonant pulse systems can be used as described in U.S. Pat. No. 5,057,776. A charged capacitor can be placed across the polarizing coils 11 to produce a half cycle at the resonant frequency to polarize the magnetic moments. Alternatively, the rising and/or falling segments 43 and 42 can be made a quarter cycle of a sinusoid by using a resonant system.

What is claimed is:

1. In a method for imaging a selected region of the body representing a relatively small portion of the anatomy using MRI the steps of: magnetizing the moments in the selected region using a pulsed super-conducting coil creating a field of greater than 2 Tesla (20 kilogauss); and receiving MRI signals from the selected region using a readout magnet providing a substantially uniform field over the selected region.

2. In a method for imaging a selected region of the body using MRI the steps of:

magnetizing the moments in the selected region using a pulsed super-conducting coil; and receiving MRI signals from the selected region using a readout magnet having an axis perpendicular to that of the pulsed super-conducting coil.

3. The method as described in claim 1 or 2 where the step of magnetizing using a pulsed super-conducting coil includes the step of recovering the stored energy of the coil following the pulse and using that energy to provide a subsequent magnetizing pulse.

4. Apparatus for imaging a selected region of the body using MRI comprising:

means for magnetizing the moments in the selected region using a pulsed super-conducting coil; and means for receiving MRI signals from the selected region using a readout magnet having an axis perpendicular to that of the pulsed super-conducting coil.

5. Apparatus for imaging a selected region of the body using MRI comprising:

means for magnetizing the moments in the selected region using a pulsed super-conducting coil; and means for receiving MRI signals from the selected region using a magnet consisting of a pair of flat readout coils on either side of the body.

6. Apparatus for imaging a selected region of the body representing a relatively small portion of the anatomy using MRI comprising:

means for magnetizing the moments in the selected region using a pulsed super-conducting coil creating a field of greater than 2 Tesla (20 kilogauss); and means for receiving MRI signals from the selected region using a readout magnet providing a substantially uniform field over the selected region.

7. Apparatus as described in claim 4 or 5 further comprising means for recovering the stored energy of the super-conducting coil following the pulse and using that energy to provide a subsequent magnetizing pulse.

8. Apparatus as described in claim 7 where the means for recovering the stored energy includes a capacitor which is first energized then used to energize the superconductive coil and then re-energized by removing the stored energy from the superconductive coil.

9. Apparatus as described in claim 8 including a switching system for reversing the polarity of the capacitor when changing from energizing the coil to re-energizing the capacitor.

10. Apparatus as described in claim 8 where the capacitor consists of an array of smaller capacitors which are connected in parallel during the energizing time of the coil and in series during the de-energizing time of the coil whereby the de-energizing time becomes shorter than the energizing time.

* * * * *